(12) United States Patent
Al-Qasim et al.

(10) Patent No.: US 11,566,519 B2
(45) Date of Patent: Jan. 31, 2023

(54) LASER-BASED MONITORING TOOL

(71) Applicant: Saudi Arabian Oil Company, Dhahran (SA)

(72) Inventors: Abdulaziz S. Al-Qasim, Dammam (SA); Sameeh Issa Batarseh, Dhahran (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 353 days.

(21) Appl. No.: 16/816,583

(22) Filed: Mar. 12, 2020

(65) Prior Publication Data

US 2021/0285325 A1 Sep. 16, 2021

(51) Int. Cl.
| | |
|---|---|
| *E21B 49/08* | (2006.01) |
| *E21B 21/00* | (2006.01) |
| *G01N 21/3504* | (2014.01) |
| *G01N 21/39* | (2006.01) |
| *G01N 33/00* | (2006.01) |

(52) U.S. Cl.
CPC .......... *E21B 49/081* (2013.01); *E21B 21/002* (2013.01); *E21B 49/088* (2013.01); *E21B 49/0875* (2020.05); *G01N 21/3504* (2013.01); *G01N 21/39* (2013.01); *G01N 33/004* (2013.01)

(58) Field of Classification Search
None
See application file for complete search history.

(56) References Cited

U.S. PATENT DOCUMENTS

| | | | |
|---|---|---|---|
| 7,635,845 B2 | 12/2009 | Jensen et al. | |
| 8,445,841 B2 | 5/2013 | Szobota et al. | |
| 9,377,449 B2 | 6/2016 | Tour et al. | |
| 9,568,419 B2 | 2/2017 | DeGreeve et al. | |
| 10,234,437 B2 | 3/2019 | Bright | |
| 2002/0152806 A1* | 10/2002 | Boucher | E21B 47/08 73/152.43 |

(Continued)

FOREIGN PATENT DOCUMENTS

WO WO-2021/181145 A1 9/2021

OTHER PUBLICATIONS

International Search Report for PCT/IB2020/055981, 4 pages (dated Dec. 1, 2020).

(Continued)

*Primary Examiner* — Edwin C Gunberg
(74) *Attorney, Agent, or Firm* — Osha Bergman Watanabe & Burton LLP

(57) ABSTRACT

An example $CO_2$ monitoring systems is configured for monitoring levels of $CO_2$ in a wellbore. A $CO_2$ monitoring system may include one or more laser monitoring tools. A laser monitoring tool may include an optical element to output a laser beam, a detector to receive the laser beam, a first chamber housing the optical element and detector, and a second chamber including an inlet and an outlet receive and release, respectively, wellbore fluid. The first chamber may be in fluid connection with second chamber via a gas permeable membrane. Gas may permeate from second chamber into first chamber. Gas in the first chamber is subjected to a laser beam. Absorption of light by the gas is measured, and content of gas is determined based at least in part on the amount of light absorption by the gas.

15 Claims, 5 Drawing Sheets

(56) References Cited

U.S. PATENT DOCUMENTS

| | | |
|---|---|---|
| 2006/0202122 A1 | 9/2006 | Gunn et al. |
| 2006/0266108 A1* | 11/2006 | DiFoggio ............... E21B 49/08 |
| | | 73/152.16 |
| 2011/0029273 A1 | 2/2011 | Lovell |
| 2012/0137764 A1 | 6/2012 | Lawrence et al. |
| 2015/0050741 A1 | 2/2015 | Tour et al. |
| 2016/0108687 A1* | 4/2016 | Rapoport ............... G01V 5/045 |
| | | 702/9 |

OTHER PUBLICATIONS

Written Opinion for PCT/IB2020/055981, 13 pages (dated Dec. 1, 2020).

Written Opinion of the International Preliminary Examining Authority for PCT/IB2020/055981, 7 pages (dated Feb. 16, 2022).

* cited by examiner

LASER-BASED MONITORING TOOL

TECHNICAL FIELD

This specification describes example implementations of a tool for performing testing of fluids in a wellbore.

BACKGROUND

Generally, there are three types of oil extraction and recovery from an oil well, namely primary, secondary, and tertiary recovery. During the primary recovery stage, hydrocarbons may be driven from a well through one or more natural mechanisms, for example, water displacing oil, expansion of natural gas in a reservoir, or gravity drainage resulting from the movement of oil within the reservoir. During the secondary recovery stage, external energy is provided to a reservoir, for example, through injecting fluids into a wellbore or rock formation to increase reservoir pressure, which increases or replaces the natural reservoir drive. During the tertiary or enhanced oil recovery (EOR) stage, thermal methods or chemical methods (or combinations of both) may be used, for example, to reduce viscosity of oil for easier recovery from a well. One example method is carbon dioxide ($CO_2$) flooding, during which $CO_2$ is injected into a reservoir where $CO_2$ mixes with oil, which reduces the viscosity of oil.

Monitoring and surveillance (M&S) programs must be in place for any $CO_2$-EOR project to obtain data and evaluate its performance. One of main objectives of the monitoring program include assessment of the storage of $CO_2$ within an oil reservoir and identify any out-of-zone $CO_2$ leakage.

SUMMARY

An example system is configured to operate within a wellbore of a hydrocarbon-bearing rock formation. The system includes one or more optical transmission media. The one or more optical transmission media may be part of an optical path originating at a laser beam generator that is configured to generate a laser beam. The one or more optical transmission media are for passing the laser beam. The system includes an optical element that is part of the optical path, the optical element for receiving the laser beam from the one or more optical transmission media and for outputting the laser beam. The system includes a detector configured and positioned to receive the laser beam output from the optical element be to detect light intensity of the laser beam. The system includes a first chamber enclosing the optical element and the detector. The system includes a second chamber in a fluid connection with the first chamber, the second chamber having a fluid inlet and a fluid outlet. The system includes a gas-permeable membrane positioned across the fluid connection such that the gas-permeable membrane forms an interface between the first chamber and second chamber.

The first chamber may include one or more $CO_2$ sniffers. The system may include a laser flow meter connected to the first chamber or second chamber. The system may include two or more laser beam generators to provide two or more laser beams. The system may include a laser flow meter connected to the first chamber or second chamber. The system may include one or more sample collection device to collect and store a solid material sample. The second chamber may be or include one or more sample collection device to collect and store a solid material sample. The system may include one or more laser tools configured to irradiate a section of a wellbore to produce a solid sample. The system may include one or more formation evaluation logging tools for calibration of wellbore depth or wellbore fluid flow parameters. The one or more formation evaluation logging tools may include one or more calipers to measure a wellbore diameter.

An example method for fluid monitoring is performed in a wellbore. The method includes providing, in a wellbore, a laser beam generator to provide a laser beam in the infrared or near-infrared spectrum. The method includes providing an optical element that is part of the optical path. The optical element is for receiving the laser beam from the one or more optical transmission media and for outputting the laser beam. The method includes providing a detector configured and positioned to receive the laser beam output from the optical element to detect light intensity of the laser beam. The method includes providing a first chamber enclosing the optical element and the detector. The method includes providing a second chamber in a fluid connection with the first chamber. The second chamber has a fluid inlet and a fluid outlet. The method includes providing a gas-permeable membrane positioned across the fluid connection such that the gas-permeable membrane forms an interface between the first chamber and second chamber. The method includes receiving, by the second chamber, wellbore fluid through the fluid inlet. The method includes receiving, by the first chamber, gas permeating through the gas-permeable membrane from the second chamber into the first chamber. The method includes subjecting the gas to the laser beam output by the optical element. The method includes receiving, by the detector, the laser beam output by the optical element. The method includes receiving intensity data from the detector. The method includes determining an amount of absorption of light of the laser beam by the gas. The method includes releasing, by the second chamber, wellbore fluid through the fluid outlet The method may include determining an amount of $CO_2$ in the gas using one or more $CO_2$ sniffers. The method may include providing two or more laser sources to provide two or more laser beams. The method may include measuring fluid flow in the wellbore using one or more laser flow meters connected to the first chamber or second chamber. The method may include retrieving a solid sample and storing the sample in sample collection device, where the second chamber is or includes the sample collection device. The method may include irradiating a section of a wellbore using one or more laser drilling tools, thereby producing a solid sample. The method may include determining wellbore depth or wellbore fluid flow parameters using one or more formation evaluation logging tools. The method may include measuring wellbore diameter using one or more calipers included in the one or more formation evaluation logging tools.

At least part of the processes and systems described in this specification may be controlled by executing, on one or more processing devices, instructions that are stored on one or more non-transitory machine-readable storage media. Examples of non-transitory machine-readable storage media include, but are not limited to, read only memory, an optical disk drive, memory disk drive, or random access memory. At least part of the processes and systems described in this specification may be controlled using a computing system comprised of one or more processing devices and memory storing instructions that are executable by the one or more processing devices to perform various control operations.

The details of one or more implementations are set forth in the accompanying drawings and the description. Other features and advantages will be apparent from the description and drawings, and from the claims.

DETAILED DESCRIPTION

Figure 1:
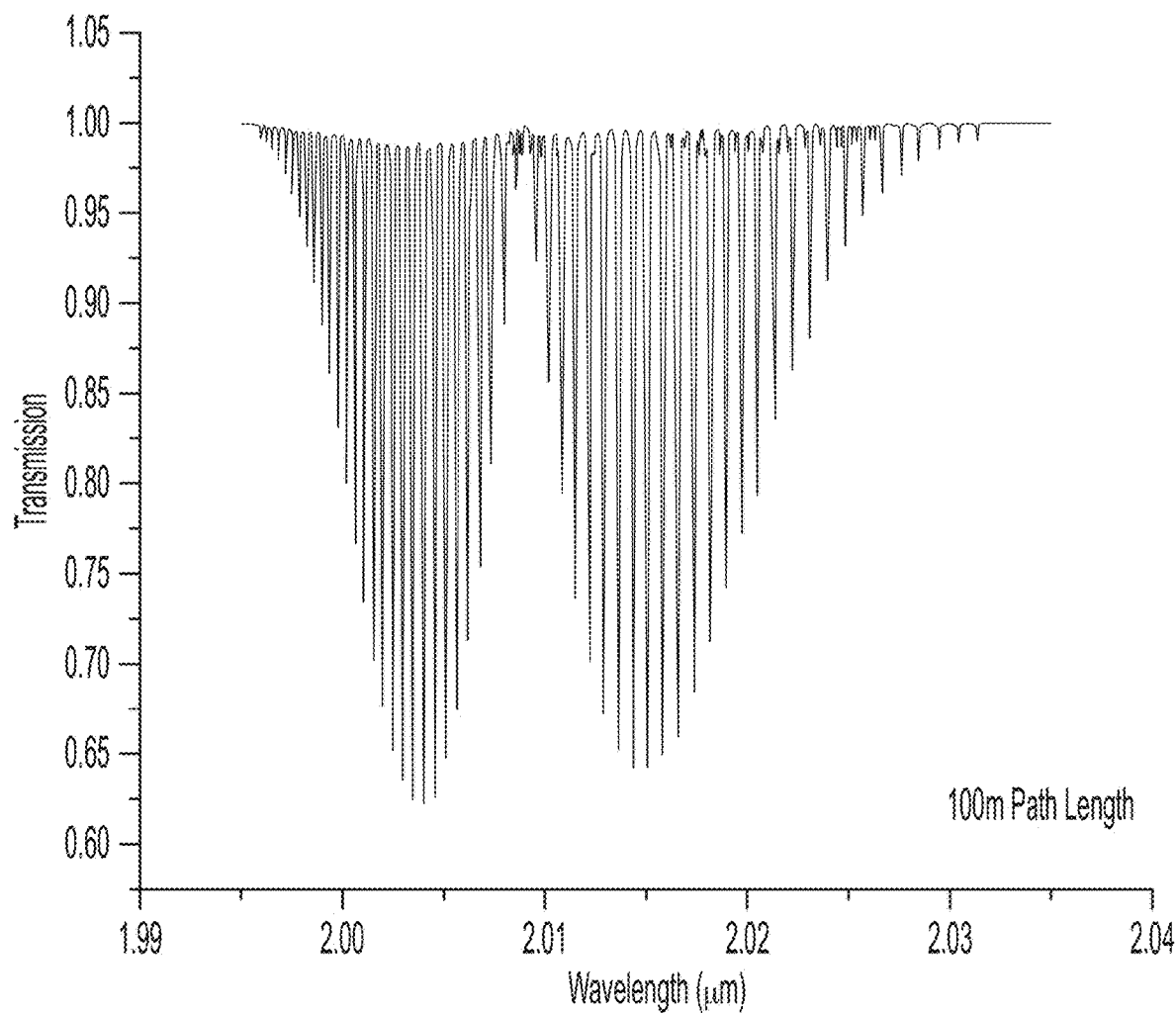
FIG. 1 shows absorption spectra of carbon dioxide near 2 microns (from Seth D. Humphries, et al.: "Atmospheric Carbon Dioxide Measurements Using a Tunable Laser Based System", Proceedings of the Carbon Sequestration Conference (2007)).

This specification describes examples of a gas monitoring system for downhole operations in an oil well. For example, a gas monitoring system may be used to monitor carbon dioxide ($CO_2$) levels in a borehole of an oil well. The system may be used to monitor $CO_2$ concentrations in gases, fluids, solids, or combinations, such as multiphase fluids.

There are currently numerous techniques and methods available for monitoring gas, for example, $CO_2$, including geochemical sampling and analyses, shallow sampling (analyzing samples retrieved from about 1-3 meters depth), and $CO_2$ sampling using $CO_2$ sniffers. These techniques, however, may have significant drawbacks: geochemical sampling, for example, may require retrieving a sample from a wellbore. The sample is then transferred and processed off-site for chemical analysis, rendering this process laborious and costly. For $CO_2$ sampling, a so-called $CO_2$ sniffer may be used. Generally, a $CO_2$ sniffer includes of an optical micro probe (sensor) or $CO_2$ analyzer. This sensor may include an infrared light source, for example, a Light-Emitting Diode (LED). Infrared light is shone through a gas sample onto a detector, which detects absorbance of light in the 4.26 micron band, which is characteristic of $CO_2$. In some implementations, a sniffer may detect $CO_2$ concentrations in the range of 0 to 20 grams per meter$^3$ (g/m$^3$) $CO_2$. The robust design of sniffer makes it flexible and easily deployable for sniffing on wells, tubing-casing annulus (TCA). A sniffer for downhole operation may be made from materials that are suitable for the harsh downhole environment, for example, pressure exceeding 15 bar and temperatures exceeding 60 degrees Celsius. A potential disadvantage of a $CO_2$ sniffer is, however that this type of device only works with gas rather than liquids or multiphase mixtures.

This specification describes a simpler and yet robust technology based on optical monitoring of analytes present in downhole fluids, for example, $CO_2$ content in a wellbore liquid or gas. In some implementations, the technology is based on the absorbance of $CO_2$ molecules by light at specific wavelengths, for example, when molecules are subjected to laser light. Example systems may be or may include stand-alone systems or they may be integrated into existing downhole system. In some implementations, an example system may be built into an oil well or rig (permanent) or may be portable, for example, for surface/subsurface shallow well monitoring. Existing downhole systems may include one or more laser tools, such as a logging tool or a wellbore stimulation tool. As explained in more detail in this specification, the described technologies provide downhole measurements for $CO_2$ or other substances that exhibit spectra that fall within an identifiable wavelength range and may provide continuous profiling along the depth of a wellbore. The technologies described in this specification may also provide flow profiling, for example, in the presence of debris or in corrosive environments. The technologies described in this specification may provide fluid or solid sample preparation and retrieval from a wellbore. The technologies described in this specification may reduce the necessity for costly logging operations by providing key information on downhole conditions using a simple and robust tool.

Figure 2:
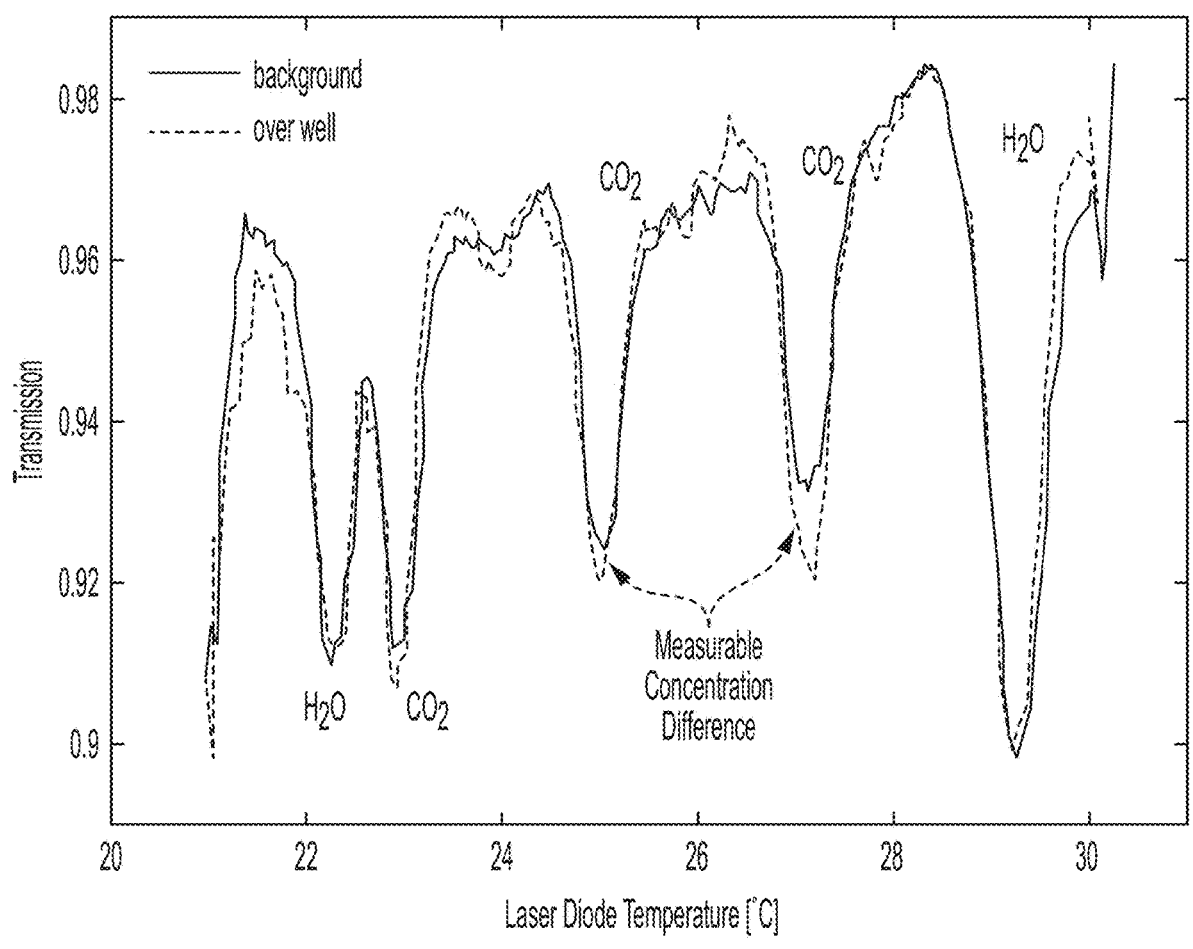
FIG. 2 shows absorption of carbon dioxide as a function of diode temperature. (from Seth D. Humphries, et al.: "Atmospheric Carbon Dioxide Measurements Using a Tunable Laser Based System", Proceedings of the Carbon Sequestration Conference (2007)).

It has been reported in the literature that $CO_2$ has a strong absorption band near a wavelength of two microns, which may allow optical remote detection for monitoring $CO_2$ at sequestration sites. FIG. 1 shows absorption spectra of carbon dioxide with strong absorption of light of wavelengths of approximately 2.0-2.02 microns (from Seth D. Humphries, et al.: "Atmospheric Carbon Dioxide Measurements Using a Tunable Laser Based System", Proceedings of the Carbon Sequestration Conference (2007)). The graph shows absorption of laser energy at 2 microns: there are two peaks identified where the transmission (opposite of absorption) decreases from 1 to 0.63. Therefore, an example surface or subsurface $CO_2$ monitoring system or device as described in this specification may be devised to measure optic axis to detect refraction and laser beam absorption by $CO_2$, using a laser system, for example, a tunable diode laser. In some implementations, example systems may be used to detect $CO_2$ concentration in a fluid, for example, a gas, in a wellbore. Due to the varying conditions downhole, for example, variations in temperature, the system may be calibrated to account for variations in system temperature, for example, the temperature of a laser diode. FIG. 2 shows absorption of carbon dioxide as a function of diode temperature, indicating variability in detection of absorbance as a function of diode temperature. (from Seth D. Humphries, et al.: Atmospheric Carbon Dioxide Measurements Using a Tunable Laser Based System). Temperature calibration may improve accuracy of the system. In some implementations, a $CO_2$ monitoring system as described in this specification may have the capability of reading/reporting the $CO_2$ concentration, in parts per million.

Figure 3:
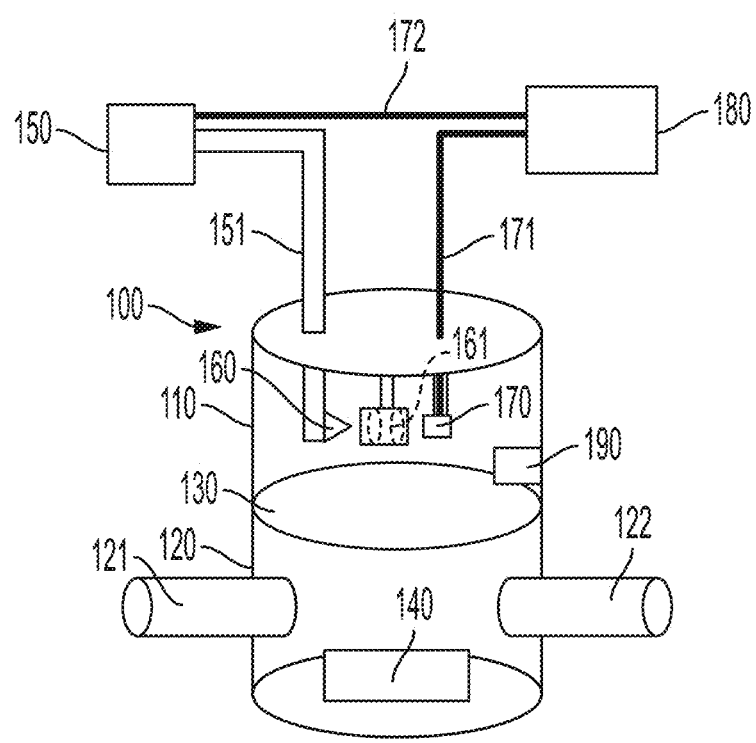
FIG. 3 is a cut-away side view of an example laser monitoring tool with two chambers.

This specification describes example $CO_2$ monitoring systems for monitoring levels of $CO_2$ in a wellbore. An example $CO_2$ monitoring system may include one or more laser monitoring tools, for example, as shown in FIG. 3. A laser monitoring tool may include an optical element 160 to output a laser beam, a detector 170 to receive the laser beam, a first chamber 110 housing the optical element 160 and detector 170, and a second chamber 120 including an inlet 121 and an outlet 122 receive and release, respectively, wellbore fluid. First chamber 110 may be in fluid connection with second chamber 120, for example, via a gas permeable membrane 130. Gas may permeate from second chamber 120 into first chamber 110. Gas in the first chamber is subjected to a laser beam. Absorption of light by the gas is measured and $CO_2$ content of gas is determined based at least in part on the amount of absorption.

A $CO_2$ monitoring system may include one or more laser monitoring tools 100, for example, as shown in FIG. 3. In some implementations, a laser monitoring tool 100 may include a chamber 110 to house one or more gas detection implements and to provide a controlled (for example, pressure controlled) environments for detection of one or more gases in a fluid. In some implementations, an example laser monitoring tool 100 includes two or more chambers. In some implementations, an example laser monitoring tool 100 includes a first chamber 110 and a second chamber 120 in fluid connection to each other. In some example implementations, first chamber 110 and second chamber 120 may be positioned adjacent and in direct contact with each other, for example, as shown in FIG. 3. In some implementations, first chamber 110 and second chamber 120 may be separated by a membrane, for example, gas permeable membrane 130. Gas permeable membrane 130 may be configured to allow passage of gas from second chamber 120 to first chamber 110 while preventing passage of liquids or solids. In some implementations, first chamber 110 and second chamber 120 may be connected via a fluid conduit (not shown). Gas permeable membrane may be positioned across said fluid conduit. In some implementations, second chamber 120 may include a fluid inlet 121 and a fluid outlet 122 to allow for entry and exit, respectively, of wellbore fluid. In some implementations, fluid inlet 121 may include a filter to prevent entry of solid debris into chamber 120.

In some implementations, a $CO_2$ monitoring system may include or may be connected to a laser system including, for example, one or more laser beam generators 150, configured to output a laser beam. In some implementations, a laser beam generator 150 is at the surface near to the wellhead. In some implementations, a laser beam generator 150 is downhole in whole or in part. An example laser beam generator 150 may be part of an optical path that includes optical element 160 and one or more optical transmission media, for example, fiber optic cable 151. Fiber optic cable 151 may be connected to an optical element 160 for receiving and outputting the laser beam to a sample fluid. Optical element 160 may be housed in first chamber 110. An optical element 160 may be at least one of a crystal, a lens, a mirror, a prism, a cube, a cylinder, or a cone. In some implementations, an optical element 160 may be or include a diode connected to an electrical energy source instead of an optical path. In some implementations, a $CO_2$ monitoring system may include two or more laser beam generators to provide separate laser beams to different components of the system. For example, a first laser beam may be provided to an optical element 160, and a second laser beam may be provided to a laser tool or a laser flow meter as described in this specification.

In some implementations, a $CO_2$ monitoring system may include or be connected to a detector element 170 to detect light output by the optical element 160. In some implementations, detector element 170 converts light received into one or more signals, for example, electrical signals. Detector element 170 may be connected to a data path, for example, data link 171, to transmit the one or more signals to a processing unit 180. In some implementations, processing unit 180 is at the surface near to the wellhead. In some implementations, processing unit 180 is downhole in whole or in part. In some implementations, processing unit 180 may include or be connected to a reference system to provide reference data, for example, pressure or temperature outside the well bore. In some implementations, processing unit 180 is connected via a data link 172 to laser beam generator 150 to control properties of the laser beam being generated, for example, beam intensity or duration.

In some implementations, one or more optical devices 161 may be positioned between optical element 160 and detection element 170. The one or more optical devices 161 may be or may include a focusing system configured to focus or to collimate the laser beam. The one or more optical devices 161 may be or include at least one of a crystal, a lens, a mirror, a prism, a cube, a cylinder, or a cone. The one or more optical devices 161 may be a structure comprised of two or more of: a crystal, a lens, a mirror, a prism, a cube, a cylinder, or a cone. In some implementations, one or more optical devices 161 may be integrated into optical element 160 forming a single unit. In some implementations, optical element 160 and detection element 170 may be configured to perform Fourier-transform infrared spectroscopy (FTIR) or Raman spectroscopy.

An example $CO_2$ monitoring system may include one or more sensors, for example, one or more sensors mounted in or on laser monitoring tool 100. In some implementations, first chamber 110 may include one or more $CO_2$ sniffers 190 mounted on an interior surface of first chamber 110. In some implementations, laser monitoring tool 100 may include one or more $CO_2$ sniffers mounted on an outside wall of the tool (not shown). In some implementations, an example $CO_2$ monitoring system may include one or more sensors to monitor environmental conditions in the wellbore and to output signals indicative of the environmental conditions. Examples of sensors may include temperature sensors to measure temperature downhole, pressure sensors to measure pressure downhole, and acoustic sensors to measure noise levels downhole. In some implementations, laser monitoring tool 100 may include one or more cameras for visual assessment of wellbore conditions.

In some implementations, laser monitoring tool 100 may include one or more $CO_2$ indicator strips. $CO_2$ indicator strips may be attached to the exterior of tool 100 or may be attached to an interior surface of the first chamber 110 or second chamber 120. In some implementations, a $CO_2$ indicator strip may include a $CO_2$ sensitive chemical substance that may, for example, react with $CO_2$ present in a contacting fluid and may cause the $CO_2$ indicator strip to change color. In some implementations, a $CO_2$ indicator strip may be sized and configured so that a color change of the strip varies along a length of the strip, thereby indicating a gradient in $CO_2$ concentration along the length of the strip. In some implementations, a plurality of $CO_2$ monitoring strips may be attached to one or more tools 100, where differences in color between strips may indicate a gradient in $CO_2$ concentration. Determination of a $CO_2$ concentration gradient may be used to determine properties (for example, direction) of a $CO_2$ plume. A $CO_2$ plume is an amount or volume of $CO_2$ that is not immobilized underground and may migrate over time. Measuring $CO_2$ concentrations at multiple locations in an underground region subjected to an oil recovery process including $CO_2$ injection, for example, measurements at one or more locations in an observation well, may show a gradient in $CO_2$ concentration across the region. A gradient across the region may indicate low sweep efficiency. Sweep efficiency relates to the effectiveness of an enhanced oil recovery process (for example, a $CO_2$ injection process) and depends on parameters including, for example, the volume of the reservoir contacted by the injected fluid, fluid injection patterns, and reservoir properties. Corrective action may be taken based on the $CO_2$ measurements. For example, gels or foams may be placed (for example, injected) into rock areas with high permeability (for example, rock areas with permeability that is elevated such that other areas are left unswept), thus redirecting flow of $CO_2$.

Figure 4:
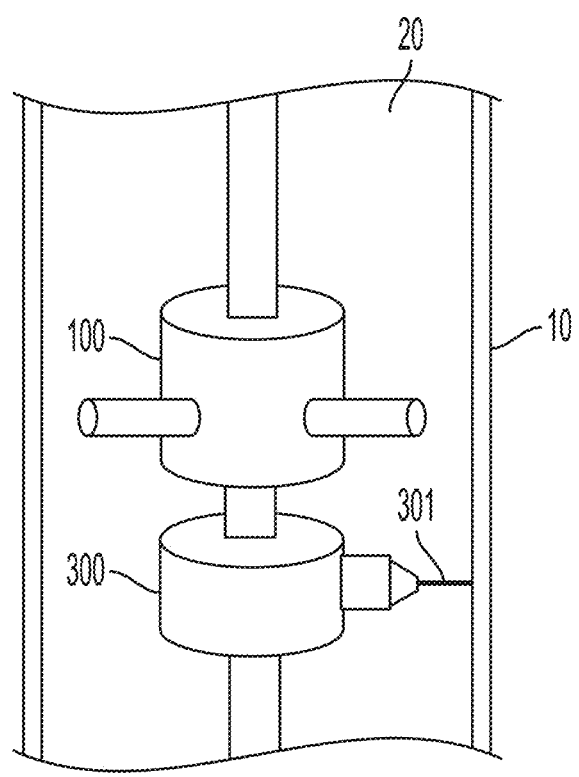
FIG. 4 is a side view of an example laser monitoring tool and a laser drilling tool suspended in a wellbore.

An example $CO_2$ monitoring system may include one or more sample collection devices 140 to collect and to store at least temporarily a gas, liquid, or solid sample. A sample may be retrieved from the wellbore and analyzed, for example, in a laboratory off site. In some implementations, one or more sample collection devices may be included in second chamber 120. Is some example implementations, a sample collection device may include, for example, a sieve or bristles to capture solid particles from a fluid stream flowing into or through second chamber 120. In some example implementations, an example $CO_2$ monitoring system may include one or more cutting or drilling implements to remove a rock sample from rock surrounding the wellbore. In some implementations, an example $CO_2$ monitoring system may be deployed with a downhole tool or tool string including a laser tool, for example, a laser drilling tool 300 outputting laser beam 301 to irradiate a section of a wall 10 of a wellbore 20, for example, as shown in FIG. 4. In some implementations, an example laser drilling tool 300 may be connected to the same optical path as a $CO_2$ monitoring system. In some implementations, a laser drilling tool may be used to drill or cut rock samples from a rock formation surrounding the wellbore, for example, to improve permeability of the rock. Rock samples separated from a rock formation may become suspended in wellbore fluid and collected from wellbore fluid entering the $CO_2$ monitoring system, for example, entering second chamber 120. In some implementations, a laser drilling tool may be used for cleanout operations in a wellbore, for example, to remove obstructions or debris from a wellbore. Such obstructions are common, particularly in arctic oil wells where low temperatures (for example, below 10 degrees Celsius) may cause formation of hydrate (natural gas, typically methane, are trapped in ice molecules), which adhere to walls in a wellbore. Solid samples separated from obstructions or debris may become suspended in wellbore fluid and collected from wellbore fluid entering the $CO_2$ monitoring system, for example, entering second chamber 120. Collected solid samples may be analyzed in the laser monitoring tool 100, for example, using laser spectroscopy.

In some implementations, solid samples, for example, rock or debris sample, may be collected using one or more sample collection implements mounted externally to laser monitoring tool 100 (not shown). Example sample collection implements include external sieves or perforated collection vessels allowing the capture of solids from fluids flowing through the sieves or collection vessels.

Figure 5:
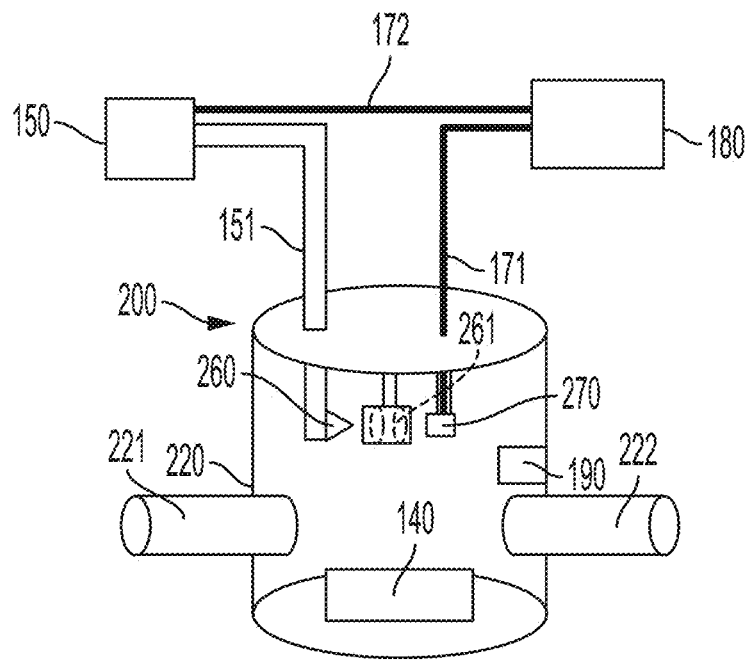
FIG. 5 is a cut-away side view of an example laser monitoring tool with a single chamber.

In some implementations, an example $CO_2$ monitoring system may include an example single chamber laser monitoring tool 200 that includes a single chamber 220 having an inlet 221 and an outlet 222 (FIG. 5). In some implementations, single chamber laser monitoring tool 200 includes the same optical path and data path components as laser monitoring tool 100. In some implementations, single chamber laser monitoring tool 200 is configured to operate in a gas filled environment, for example, in a wellbore above a level of liquid hydrocarbons or in natural gas well. In some implementations, single chamber laser monitoring tool 200 is configured to operate in a fluid filled environment, for example, in a wellbore of an oil well. Fluid, for example, a gas or a multiphase mixture, may enter chamber 220 through inlet 221 and may be analyzed as described in this specification for laser monitoring tool 100. Fluid may exit chamber 220 through outlet 222. In some implementations, single chamber laser monitoring tool 200 is configured to operate in a liquid or multiphase environment. Components of the optical path, for example, optical element 260, optical device 261, and detector 270 may be configured to operate at least partially immersed in liquid. Spectroscopic analysis may be performed directly on a liquid phase, on a gas phase, or a combination of liquid and gas. In some implementations, fluid inlet 221 may include a filter to prevent entry of solid debris into chamber 220.

In some implementations, an example $CO_2$ monitoring system may include one or more optical flow measurement devices for flow profiling in a wellbore. In some implementations, an optical flow measurement device includes a laser Doppler flow meter (or Laser Doppler Velocimetery (LDV)), which uses Doppler shift in a laser beam to measure one or more velocities in transparent or semi-transparent fluid flows. In some implementations, lasers with wavelengths from 250 to 3300 nanometers (nm) may be used for velocity measurements. Different wavelength may be used depending on the gasses or mixtures to be detected.

Laser wavelengths may be tunable for fluid measurements in production oil wells or injection wells. In production wells, a wellbore fluid is production fluid, for example, a mixture of hydrocarbons. In injections wells, water is injected into an oil field, usually to increase pressure and thereby stimulate production. A wellbore fluid in an injection well may be a mixture of hydrocarbons and water with a higher water content than in a production well fluid. In some implementations, one or more optical flow measurement devices may be connected to or attached to laser monitoring tool 100. In some implementations, one or more optical flow measurement devices may be part of same optical path or may be connected to the same optical path as laser monitoring tool 100. In some implementations, one or more optical flow measurement devices may be part of a separate optical path.

Figure 6A:
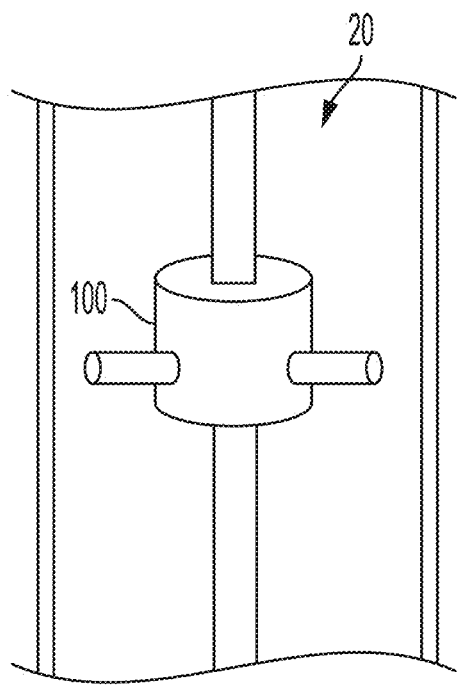
FIG. 6A is a side view of a stand-alone laser monitoring tool deployed in a wellbore.
Figure 6B:
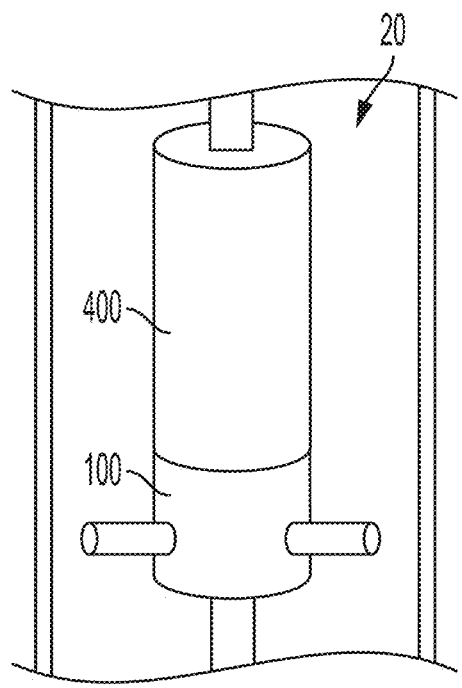
FIG. 6B is a side view of an example laser monitoring tool connected to an example logging tool deployed in a wellbore.

An example $CO_2$ monitoring system may include one or more stand-alone laser monitoring tools 100 or be connected to one or more downhole tools. In some implementations, laser monitoring tool 100 may be integrated into a downhole tool or tool string. In some implementations, an example $CO_2$ monitoring system may be equipped with, integrated with, or connected to a set of formation evaluation logging tools to measure continuously formation or wellbore properties, for example, dimensional, sonic, or electrical properties of a formation or wellbore. FIG. 6A shows a schematic of a stand-alone laser monitoring tool 100 deployed in a wellbore 20. FIG. 6B shows a schematic of an example laser monitoring tool 100 connected to an example logging tool 400 deployed in a wellbore 20. Example laser monitoring tools 100 are positioned in or on a downhole tool such that a flow to and from laser monitoring tool 100 is not obstructed, for example, such that flow paths into inlet 121 and out of outlet 122 remain unobstructed. Example laser monitoring tools 100 are positioned in or on a downhole tool such that a laser monitoring tool does not interfere with operation of the downhole tool, for example, the operation of one or more instruments on an example evaluation logging tool. Example instruments of an evaluation logging tool include calipers that measure (for example, mechanically) diameter or shape of a wellbore. Measurement and mapping of wellbore size and geometry together with laser fluid velocity measurements (as described in this specification) may provide input information for calculation of wellbore flow rates. In some implementations, an example $CO_2$ monitoring system may be connected to or may be integrated into a production logging tool (PLT). A PLT may be used to record one or more measurements that describe the nature and behavior of fluids in or around the borehole during hydrocarbon production or (water) injection into an oil field. Addition or integration of an example $CO_2$ monitoring system may extend the capability of a conventional PLT, for example, to capture three-phase fluid profile of a wellbore fluid.

Conventional PLTs often include mechanical and moving parts for fluid measurements, for example, spinner flow meters. Spinner flow meters measure fluid velocity based on the speed of rotation of an impeller (or spinner) exposed to wellbore fluid. Presence of wax, sludge, or other solids may occlude the impeller, impeding flow measurements in wellbore intervals where such impediments are present in the wellbore fluid. In some implementations, optical flow measurement devices, for example, laser based optical flow measurement devices as described in this specification, may be used alone or in combination with spinner flow meters and may provide fluid velocity data in cases a spinner flowmeter is damaged due to wax or other downhole conditions. In some implementations, optical flow measurement devices are made of corrosion resistant material or are coated with corrosion resistant material (for example, ceramics). These corrosion resistant properties allow capturing of flow profile in corrosive environments.

An example laser based gas monitoring set up was evaluated in a laboratory experiment. For the laboratory experiment, a commercially available Perkin Elmer® Lambda 950 Ultraviolet-Visible-Infrared (UV-VIS-IR) wideband spectrophotometer was used. This spectrophotometer may be used to characterize the transmittance, reflectance, and absorbance of fluids, solids, and powders. Spectrometers can work in transmission or reflection mode. In transmission mode, light of a known frequency is passed through the sample, and a photodetector measures, for example, the amount of light transmitted. In reflection mode, a light probe illuminates a target sitting in an integrating sphere. The reflected light is then collected and measured by a photodetector that measures, for example, the intensity of the reflected light. Thus, a spectrophotometer device measures optical (UV, visible, IR) transmission, reflection and absorption properties of a range of subsurface matter, including rock, oil, brine, and multiphase compounds.

Figure 7:
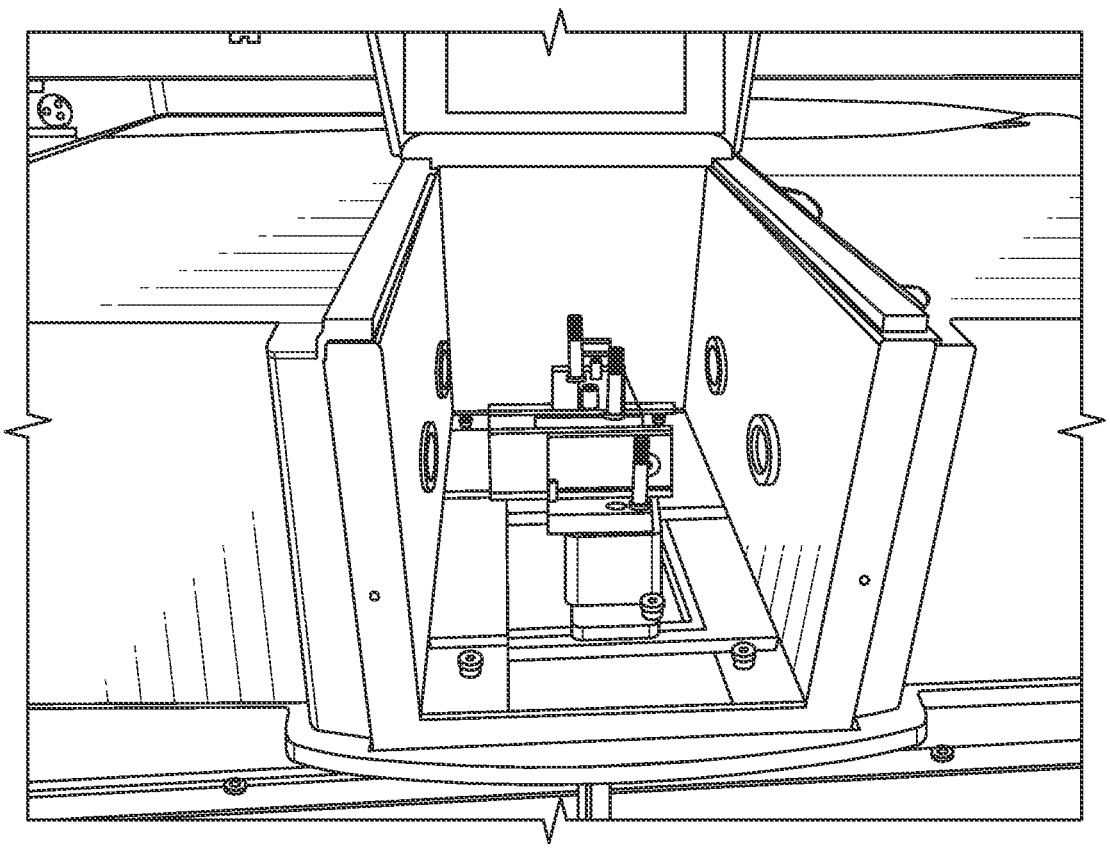
FIG. 7 depicts a spectrophotometer set up used in a laboratory experiment.
Figure 8A:
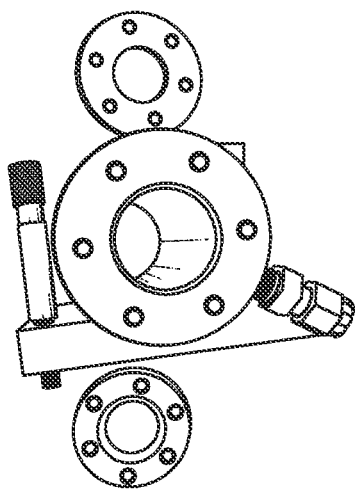
FIG. 8A is a top view and FIG. 8B is a side view of an example custom designed chamber for spectrophotometry experiments.
Figure 8B:
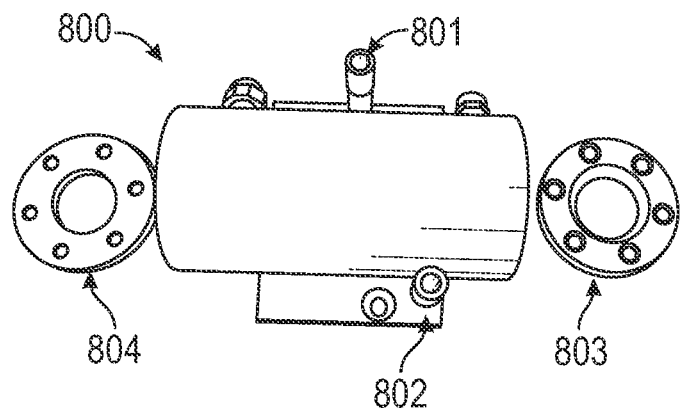

FIG. 7 depicts a spectrophotometer as used for laboratory experiments. The device includes light sources to cover a wavelength range spanning from 240 nm to 3300 nm and houses different attachments for characterization: ISR-3100/1503 Integrating Sphere Attachment (220 nm-2600 nm) for reflectance characterization (diffuse and specular); MPC-603 Multi-Purpose Large-Sample Compartment (240 nm-2600 nm) for reflectance and transmittance characterization; and liquid, solid, power sample holders. A custom designed chamber was designed for gas experiments. An example custom designed chamber 800 is shown in FIG. 8A and FIG. 8B. The design of this example chamber mimics the single chamber set-up of single chamber laser monitoring tool 200. The example design allows sample gas to flow into an enclosed chamber through a gas inlet 801 and exit the chamber through a gas outlet 802. The chamber includes two cover lenses 803 and 804 at opposing ends to allow a light beam to pass through a gas sample. For example, a light beam emitted by a light source (for example, of a spectrophotometer) may enter the chamber through the first lens, for example, lens 803. In the chamber, light is absorbed by the gas. Light exits the chamber through the second lens, for example, lens 804, and is detected by a detector, for example, in the spectrophotometer. Absorbance of light by the gas is detected by comparing intensity of light emitted with intensity of light detected.

Temperature of a light emitter, for example, a light emitting diode, may affect absorbance measurements as shown in FIG. 2. Absorbance may also be affected by temperature of the gas. Therefore, absorbance is measured under a range of different temperatures of gas or temperature of emitter to reflect various downhole conditions. A matrix to present the absorption as a function of the temperature and wavelength may then be generated.

All or part of the technologies described in this specification and their various modifications can be implemented or controlled, at least in part, via a computer program product, such as a computer program tangibly embodied in one or more information carriers, such as in one or more tangible machine-readable storage media, for execution by, or to control the operation of, data processing apparatus, such as a programmable processor, a computer, or multiple computers.

A computer program can be written in any form of programming language, including compiled or interpreted languages, and it can be deployed in any form, including as a stand-alone program or as a module, part, subroutine, or other unit suitable for use in a computing environment. A computer program can be deployed to be executed on one computer or on multiple computers at one site or distributed across multiple sites and interconnected by a network.

Actions associated with operating or controlling the tools can be performed or controlled by one or more programmable processors executing one or more computer programs to perform the functions of the calibration process. All or part of the tools can be controlled using special purpose logic circuitry, for example, an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only storage area or a random access storage area or both. Elements of a computer (including a server) include one or more processors for executing instructions and one or more storage area devices for storing instructions and data. Generally, a computer will also include, or be operatively coupled to receive data from, or transfer data to, or both, one or more machine-readable storage media, such as mass storage devices for storing data, for example, magnetic, magneto-optical disks, or optical disks. Non-transitory machine-readable storage media suitable for embodying computer program instructions and data include all forms of non-volatile storage area, including by way of example, semiconductor storage area devices such as erasable programmable read-only memory, electrically erasable programmable read-only memory, and flash storage area devices; magnetic disks such as internal hard disks or removable disks; magneto-optical disks; and CD-ROM and DVD-ROM disks.

Each computing device, such as server, may include a hard drive for storing data and computer programs, and a processing device (for example, a microprocessor) and memory (for example, RAM) for executing computer programs.

Elements of different implementations described in this specification may be combined to form other implementations not specifically set forth above. Elements may be left out of the tools and associated components described in this specification without adversely affecting their operation or the operation of the system in general. Furthermore, various separate elements may be combined into one or more individual elements to perform the functions described in this specification.

Other implementations not specifically described in this specification are also within the scope of the following claims.

What is claimed:

1. A system configured to operate within a wellbore of a hydrocarbon-bearing rock formation, the system comprising:
one or more optical transmission media, the one or more optical transmission media being part of an optical path originating at a laser beam generator configured to generate a laser beam, the one or more optical transmission media for passing the laser beam;
an optical element that is part of the optical path, the optical element for receiving the laser beam from the one or more optical transmission media and for outputting the laser beam;
a detector configured and positioned to receive the laser beam output from the optical element be to detect light intensity of the laser beam;
a first chamber enclosing the optical element and the detector;
a second chamber in a fluid connection with the first chamber, the second chamber having a fluid inlet and a fluid outlet;
one or more sample collection devices to collect and store a solid material sample; and
a gas-permeable membrane positioned across the fluid connection such that the gas-permeable membrane forms an interface between the first chamber and second chamber.

2. The system of claim 1, where first chamber comprises one or more $CO_2$ sniffers.

3. The system of claim 1, comprising a laser flow meter connected to the first chamber or second chamber.

4. The system of claim 1, comprising two or more laser beam generators to provide two or more laser beams.

5. The system of claim 1, where the second chamber is or comprises one or more sample collection device to collect and store a solid material sample.

6. The system of claim 1, comprising one or more laser tools configured to irradiate a section of a wellbore to produce a solid sample.

7. The system of claim 1, comprising one or more formation evaluation logging tools for calibration of wellbore depth or wellbore fluid flow parameters.

8. The system of claim 7, where the one or more formation evaluation logging tools comprise one or more calipers to measure a wellbore diameter.

9. A method for wellbore monitoring comprising:
providing, in a wellbore, a laser beam generator to provide a laser beam in the infrared or near-infrared spectrum;
providing an optical element that is part of the optical path, the optical element for receiving the laser beam from the one or more optical transmission media and for outputting the laser beam;
providing a detector configured and positioned to receive the laser beam output from the optical element to detect light intensity of the laser beam;
providing a first chamber enclosing the optical element and the detector;
providing a second chamber in a fluid connection with the first chamber, the second chamber having a fluid inlet and a fluid outlet;
providing a gas-permeable membrane positioned across the fluid connection such that the gas-permeable membrane forms an interface between the first chamber and second chamber;
receiving, by the second chamber, wellbore fluid through the fluid inlet;
retrieving a solid sample and storing the sample in a sample collection device, where the second chamber is or comprises the sample collection device;
receiving, by the first chamber, gas permeating through the gas-permeable membrane from the second chamber into the first chamber;
subjecting the gas to the laser beam output by the optical element;
receiving, by the detector, the laser beam output by the optical element;
receiving, by a processing unit, intensity data from the detector;
determining, by a processor of the processing unit, an amount of absorption of light of the laser beam by the gas; and
releasing, by the second chamber, wellbore fluid through the fluid outlet.

10. The method of claim 9, comprising determining an amount of $CO_2$ in the gas using one or more $CO_2$ sniffers.

11. The method of claim 9, comprising providing two or more laser sources to provide two or more laser beams.

12. The method of claim 9, comprising measuring fluid flow in the wellbore using one or more laser flow meters connected to the first chamber or second chamber.

13. The method of claim 9, comprising irradiating a section of a wellbore using one or more laser drilling tools, thereby producing a solid sample.

14. The method of claim 9, comprising determining wellbore depth or wellbore fluid flow parameters using one or more formation evaluation logging tools.

15. The method of claim 9, comprising measuring wellbore diameter using one or more calipers included in the one or more formation evaluation logging tools.

* * * * *